US00RE46189E

(19) United States
(12) Reissued Patent
Prichep et al.

(10) Patent Number: US RE46,189 E
(45) Date of Reissued Patent: Nov. 1, 2016

(54) FIELD DEPLOYABLE CONCUSSION ASSESSMENT DEVICE

(71) Applicants: Brainscope Company, Inc., Bethesda, MD (US); New York University, New York, NY (US)

(72) Inventors: Leslie S. Prichep, Mamaroneck, NY (US); Neil S. Rothman, Baltimore, MD (US); Douglas C. Oberly, South Windsor, CT (US); Michael E. Singer, Bethesda, MD (US)

(73) Assignees: Brainscope Company, Inc., Bethesda, MD (US); New York University, New York, NY (US)

(21) Appl. No.: 14/747,538

(22) Filed: Jun. 23, 2015

Related U.S. Patent Documents

Reissue of:
(64) Patent No.: 8,478,394
Issued: Jul. 2, 2013
Appl. No.: 12/857,504
Filed: Aug. 16, 2010

(51) Int. Cl.
*A61B 5/04* (2006.01)

(52) U.S. Cl.
CPC ..... *A61B 5/04004* (2013.01); *A61B 5/04* (2013.01)

(58) Field of Classification Search
None
See application file for complete search history.

(56) References Cited

U.S. PATENT DOCUMENTS 6,826,509 B2 * 11/2004 Crisco, III ..... A42B 3/046 2/422
7,526,389 B2 * 4/2009 Greenwald ..... A42B 3/046 2/425
7,904,144 B2 * 3/2011 Causevic ..... A61B 5/048 600/544
8,364,254 B2 * 1/2013 Jacquin ..... A61B 5/0476 600/544
8,382,485 B2 * 2/2013 Bardsley ..... 434/262
8,478,394 B2 * 7/2013 Prichep ..... A61B 5/0478 128/920
8,548,768 B2 * 10/2013 Greenwald ..... A61B 5/0002 340/573.1
8,554,509 B2 * 10/2013 Crisco, III ..... A42B 3/046 2/425

(Continued)

FOREIGN PATENT DOCUMENTS

WO 2007/016149 A2 2/2007
WO 2009/111426 A1 9/2009
WO 2010/088252 A1 8/2010

OTHER PUBLICATIONS

Besserve, et al. "Classification Methods for Ongoing EEG and MEG Signals", Biol. Res. vol. 40, No. 2007, pp. 415-437. (XP-002613523).

(Continued)

*Primary Examiner* — Glenn K Dawson
(74) *Attorney, Agent, or Firm* — Finnegan, Henderson, Farabow, Garrett & Dunner, LLP

(57) ABSTRACT

A device and method for assessment of traumatic brain injury (TBI) is described. The device is configured to acquire brain electrical signals from a patient's forehead using one or more neurological electrodes. The acquired brain electrical activity data is subjected to artifact rejection and feature extraction, and a subset of features are then combined in at least one classifier function. The classifier functions statistically place a patient in one of four categories related to the extent of brain dysfunction: 1) normal brain electrical activity; 2) abnormal brain electrical activity consistent with non-structural injury with less severe manifestations of functional brain injury; 3) abnormal brain electrical activity consistent with non-structural injury with more severe manifestations of functional brain injury; and 4) abnormal brain electrical activity consistent with structural brain injury.

15 Claims, 8 Drawing Sheets

(56) References Cited

U.S. PATENT DOCUMENTS

| | | | | |
|---|---|---|---|---|
| 8,797,165 | B2 * | 8/2014 | Greenwald | A61B 5/0002 2/411 |
| 2002/0060633 | A1 * | 5/2002 | Crisco, III | A42B 3/046 340/669 |
| 2005/0177335 | A1 * | 8/2005 | Crisco, III | A42B 3/046 702/141 |
| 2005/0177929 | A1 * | 8/2005 | Greenwald | A42B 3/046 2/425 |
| 2006/0074338 | A1 * | 4/2006 | Greenwald | A61B 5/0002 600/549 |
| 2006/0189852 | A1 * | 8/2006 | Greenwald | A61B 5/0002 600/300 |
| 2007/0032737 | A1 * | 2/2007 | Causevic et al. | A61B 5/048 600/544 |
| 2009/0000377 | A1 * | 1/2009 | Shipps | A61B 5/11 73/514.16 |
| 2009/0082689 | A1 * | 3/2009 | Guttag et al. | 600/544 |
| 2010/0191139 | A1 * | 7/2010 | Jacquin et al. | A61B 5/0476 600/544 |
| 2011/0038515 | A1 * | 2/2011 | Jacquin et al. | 382/128 |
| 2011/0125048 | A1 * | 5/2011 | Causevic | A61B 5/048 600/544 |
| 2011/0144519 | A1 * | 6/2011 | Causevic | A61B 5/0006 600/544 |
| 2011/0144520 | A1 * | 6/2011 | Causevic | A61B 5/0476 600/544 |
| 2011/0144539 | A1 * | 6/2011 | Ouchi | A42B 3/046 600/587 |
| 2014/0349984 | A1 * | 11/2014 | Hoffman | A61K 31/57 514/177 |

OTHER PUBLICATIONS

PCT International Search Report and Written Opinion mailed Nov. 15, 2011, in PCT/US2011/047533.

* cited by examiner

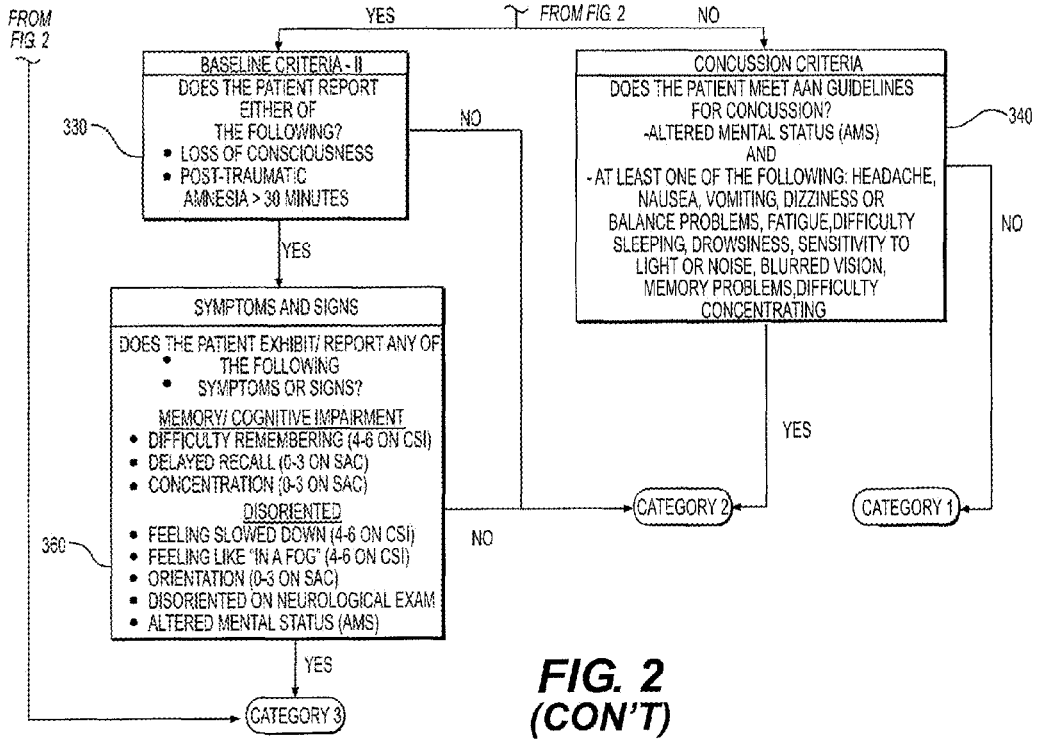
FIG. 2 (CON'T)

| CATEGORY (CLASSIFICATION) | CT SCAN (BRAIN STRUCTURE) | BRIAN ELECTRICAL ACTIVITY (BRAIN FUNCTION) | FUNCTIONAL MANIFISTATIONS (CLINICAL/BEHAVIORAL) | SENSITIVITY/SPECIFICITY OF CLASSIFICATION |
|---|---|---|---|---|
| 1 | NA | NORMAL | ABSENT | 1 vs 2,3,4<br>81/80 |
| 2 | NEGATIVE (-) OR NOT INDICARED | ABNORMAL | PRESENT (RATED MILD) | 1,2 vs. 3,4<br>80/79 |
| 3 | NEGATIVE (-) OR NOT INDICATED | ABNORMAL | PRESENT (RATED MOD-SEV) | |
| 4 | POSITIVE (+) | ABNORMAL | SALIENT FEATURE CT+ | 4 vs 3,2,1<br>91/85 |

TABLE 1

*FIG. 6*

FIELD DEPLOYABLE CONCUSSION ASSESSMENT DEVICE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*This is a reissue of U.S. Pat. No. 8,478,394, issued on Jul. 2, 2013 from U.S. patent application Ser. No. 12/857,504 filed on Aug. 16, 2010. The entire contents of each of the above-referenced applications are incorporated herein by reference.*

TECHNICAL FIELD

The present disclosure relates to the field of neurological assessment, and specifically, to a portable, handheld apparatus and method for performing neurological triage on a patient at the point-of-care.

BACKGROUND

The brain performs the most complex and essential processes in the human body. Surprisingly, contemporary health care lacks sophisticated tools to objectively assess brain function at the point-of-care. A patient's mental and neurological status is typically assessed by an interview and a subjective physical exam. Clinical laboratories currently have no capacity to assess brain function or pathology, contributing little more than identification of poisons, toxins, or drugs that may have externally impacted the central nervous system (CNS).

Brain imaging studies, such as computed tomography (CT) and magnetic resonance imaging (MRI), are widely used to visualize the structure of the brain. However, CT scan and MRI are anatomical tests and reveal very little information about brain function. For example, intoxication, concussion, active seizure, metabolic encephalopathy, infections, and numerous other conditions (e.g. diabetic coma) show no abnormality on CT scan. A classic stroke, or a traumatic brain injury (TBI), may not be immediately visualized by an imaging test even if there is a clear and noticeably abnormal brain function. Similarly, diffuse axonal injury (DAI), related to shearing of nerve fibers which is present in a majority of concussive brain injury cases, can remain invisible on most routine structural images. If undetected at an early stage, swelling or edema from DAI can subsequently lead to coma and death.

Functional MRI (fMRI) is a recent improvement over MRI, which provides relative images of the concentration of oxygenated hemoglobin in various parts of the brain. While the concentration of oxygenated hemoglobin is a useful indication of the metabolic function of specific brain regions, it provides very limited information about the underlying electrochemical processes within the brain.

Further, CT and MRI/fMRI testing devices are not field-deployable due to their size, power requirements and cost. These assessment tools play an important role in selected cases, but they are not universally available, require experienced personnel to operate, and MRI/fMRI do not provide sufficient critical information at the early stages of acute neurological conditions. Current technologies are unable to provide the immediate information critical to timely intervention, appropriate triage for the formulation of an appropriate plan of care for acute brain trauma. Unfortunately, the brain has very limited capacity for repair, and thus time-sensitive triage and intervention is very important in treating brain injuries.

Currently, emergency room patients with altered mental status, acute neuropathy, or head trauma must undergo costly and time-consuming tests to determine an appropriate diagnosis that leads to a course of treatment. Unfortunately, in many cases, the clinical condition of patients can deteriorate as they wait for equipment to become available or for specialists to either arrive and/or interpret tests offsite, such tests being inadequate to diagnose the patients' condition. The problem that faces ER physicians is that their resources are limited to a subjective physical exam, and all of the physician's decisions concerning the administration of emergency treatment, additional consultation by a neurologist, or patient discharge, are based on the results of this physical exam. Often, ER patients are sent for imaging studies, yet many functional brain abnormalities, as discussed earlier, are not visible on a CT scan or MRI. Some abnormalities which eventually have anatomical and structural consequences often take time to become visible on an imaging test. This is true for many important conditions, such as ischemic stroke, concussion/traumatic brain injury (TBI), raised intracranial pressure, and others. This indicates the need for real-time, functional brain state assessment technology, which can be performed in the ER, or in an ambulatory setting, and can detect emergency neurological conditions hours ahead of the standard clinical assessment tools available today. Also, there is a need for a point-of-care assessment tool for detection of TBI in soldiers out in the battlefield, and for detection of sports-related brain injury in athletes. A field-deployable, readily accessible, non-radiation emitting, easy-to-use brain state assessment tool could have significant impact on the successful clinical management of head injuries in the Military Health System (MHS). Similarly, rapid, on-the-field assessments of concussive head injuries could prevent repeat injuries and "second impact syndrome" in athletes already suffering from a first traumatic brain impact.

EEG (electroencephalography) technology, which is based on detecting and analyzing brain electrical activity, is accepted today in neurodiagnostics as a quantitative brain state assessment tool. However, its application in the clinical environment is notably limited. Some of the barriers limiting its adoption include: the cost of EEG equipment, the need for a skilled technician to administer the test, the time it takes to conduct the test, and the need for expert interpretation of the raw data. The instrument produces essentially raw waveforms which must be carefully interpreted by an expert. Data is collected and analyzed by an EEG technician, and is then presented to a neurologist for interpretation and clinical assessment. Further, the waveforms for many of these conditions, such as, TBI, cannot be seen by the interpreting expert without additional signal processing. This makes the currently available EEG equipment unfeasible for neuro-triage applications in emergency rooms or at other point-of-care settings. More importantly, the current technology is not field-portable (handheld) which makes it impractical for various field applications, e.g., at a battle field, or a sports field event. Thus, there is an immediate need for a handheld objective tool with real-time results based on brain electrical activity, which can provide rapid, point-of-care neurological triage and treatment guidance for patients with acute brain injury or disease.

SUMMARY

The present disclosure addresses the need for point-of-care neuro-triage by providing a portable, handheld device for objective, real-time evaluation of the brain electrical activity of a patient. A first aspect of the present disclosure includes an apparatus for assessment of traumatic brain injury in a patient. The apparatus comprises a patient sensor having at least one neurological electrode for acquiring brain electrical signals from a patient, and a handheld base unit operatively coupled to the patient sensor for processing the acquired brain electrical activity data. The base unit comprises a digital signal processor configured to perform automatic identification and removal of artifacts from the brain electrical activity data, extract one or more features from the data, and execute at least three binary classification functions to classify the patient into one of four categories indicative of the presence and severity of traumatic brain injury.

Another aspect of the present disclosure includes a method for assessment of traumatic brain injury in a patient. The method comprises the steps of connecting at least one neurological electrode to a patient's forehead to acquire brain electrical signals, and providing a handheld base unit operatively connected to the at least one neurological electrode to process the acquired brain electrical signals. The base unit comprises a digital signal processor configured to perform automatic identification and removal of artifacts from the acquired brain electrical activity data, extract one or more features from the data, and execute at least three binary classification functions to classify the patient into one of four categories indicative of the presence and severity of traumatic brain injury.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the various aspects of the invention.

BRIEF DESCRIPTION OF DRAWINGS AND TABLES

FIG. 6 is table showing classification results for each category related to the extent of TBI, in accordance with an exemplary embodiment of the present disclosure.

DESCRIPTION OF ILLUSTRATIVE EMBODIMENTS

Reference will now be made in detail to certain embodiments consistent with the present disclosure, examples of which are illustrated in the accompanying drawings. Wherever possible, the same reference numbers will be used throughout the drawings to refer to the same or like parts.

In an exemplary embodiment, data corresponding to brain electrical activity is used to detect neurological injury or disease in patients. The brain electrical signals are measured and analyzed at the point-of-care using a portable neuro-assessment device. In an exemplary embodiment of the present disclosure, a subject's brain electrical activity is recorded using a varying number of electrodes located at standardized positions on the scalp and forehead, and the subject's brain electrical signals are assessed with reference to one or more databases. For example, collected normative data, indicative of normal brain electrical activity, is used to establish quantitative features of brain electrical activity, which clearly distinguish brain signals produced in the presence and absence of acute neurological disorder. This normative dataset includes brain activity data of a control group of population. A normative population in the database comprises of individuals similar to a subject in one or more aspects, such as age, gender, etc. In one exemplary embodiment, a subject is compared to individuals in the database using a regression equation as a function of age. The collected normative database employed by the inventors has been shown to be independent of racial background and to have extremely high test-retest reliability, specificity (low false positive rate) and sensitivity (low false negative rate).

Figure 1:
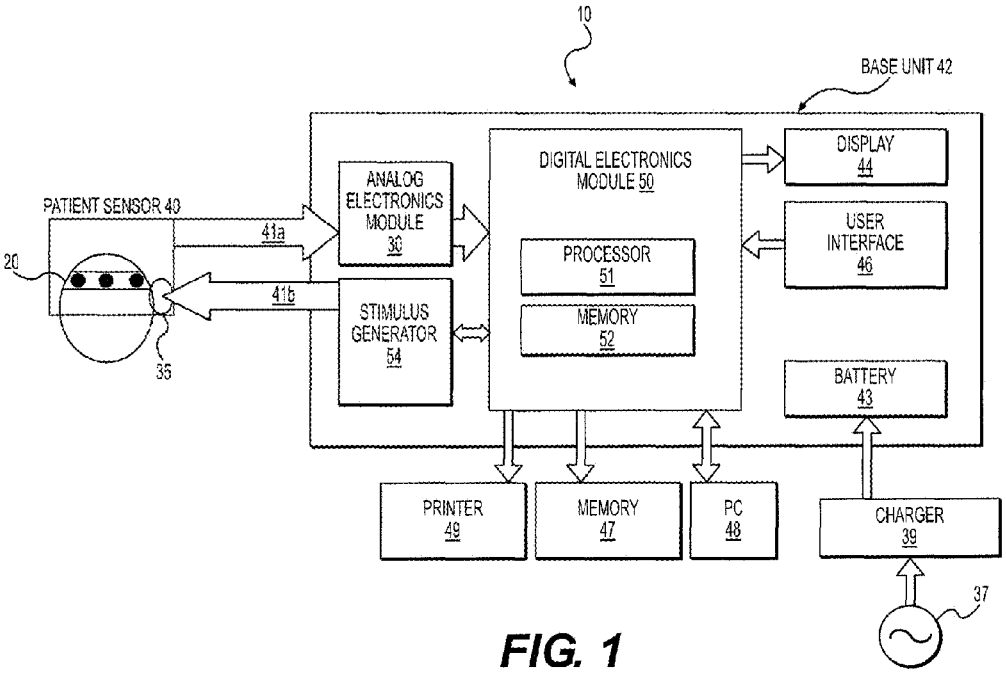
FIG. 1 is a schematic of a neuro-assessment apparatus, in accordance with an exemplary embodiment of the present disclosure.

In accordance with embodiments consistent with the present disclosure, FIG. 1 shows a neuro-assessment apparatus 10 for acquiring and processing brain electrical signals, and providing an evaluation of the patient's neurological condition. In an exemplary embodiment, neuro-assessment apparatus 10 is implemented as a portable device for point-of-care applications. This apparatus consists of a patient sensor 40 which may be coupled to a base unit 42, which can be handheld, as illustrated in FIG. 1. Patient sensor 40 may include an electrode array 20 comprising at least one disposable neurological electrode to be attached to a patient's head to acquire brain electrical signals. The electrodes are configured for sensing both spontaneous brain activity as well as evoked potentials generated in response to applied stimuli (e.g. auditory, visual, tactile stimuli, etc.). In one exemplary embodiment, the apparatus comprises of five (active) channels and three reference channels. The electrode array 20 consists of anterior (frontal) electrodes: Fp1, Fp2, F7, F8, AFz (also referred to as Fz') and Fpz (reference electrode) to be attached to a subject's forehead, and electrodes A1 and A2 to be placed on the front or back side of the ear lobes, or on the mastoids, in accordance with the International 10/20 electrode placement system (with the exception of AFz). Other electrode configurations may be utilized as and when required, as would be understood by those of ordinary skill in the art.

In one exemplary embodiment, the neuro-assessment apparatus 10 utilizes the advantages of auditory evoked potential (AEP) signals to map specific auditory, neurological and psychiatric dysfunctions. In such an embodiment, the patient sensor 40 includes an optional reusable earphone 35 to provide auditory stimuli clicks in either ear.

The patient sensor 40 also includes two reusable patient interface cables which are designed to plug into the base unit 42 and provide direct communication between the patient sensor 40 and the base unit 42. The first cable is an electrical signal cable 41a, which can be equipped with standard snap connectors to attach to the disposable electrodes placed on the patient's scalp. The second cable is the AEP stimulus cable 41b which can provide connection to the earphone 31 for auditory stimulus delivery. Other auditory stimuli may also be used, to evoke mid-latency (20-80 milliseconds) or late auditory responses (>80 milliseconds), including the P300.

The base unit 42 primarily includes an analog electronics module 30, a digital electronics module 50, user interface 46, stimulus generator 54, display 44 and battery 43, as illustrated in FIG. 1. In certain embodiments, the user interface 46 and display 44 are combined into a single input and output unit, for example, a touch screen user interface. The analog electronics module receives signals from one or more of the neurological electrodes operatively connected through the electrical cable 41a. The analog module is configured to amplify, filter, and preprocess the analog waveforms acquired from the electrodes. The analog module may comprise signal amplification channels including at least one differential amplifier, at least one common mode detector, and at least one gain stage with filter. The analog module 30 may further include a multiplexer (MUX), which combines many analog input signals and outputs that into a single channel, and an analog-to-digital converter (ADC) to digitize the received analog signal. Digital electronics module 50 can then process the digitized data acquired through analog module 30 and can perform analysis of the data to aid in interpretation of the brain electrical activity waveforms.

Referring again to FIG. 1, the digital electronics module 50 may be operatively connected with a number of additional device components. In exemplary embodiments, the digital electronics module 50 comprises a digital signal processor (DSP) 51 for processing the data corresponding to the acquired brain electrical signals, and a memory 52 which stores the instructions for processing the data, such as a DSP algorithm. The processor 51 can be configured to perform the following tasks— a) Automatic identification and removal of several types of signal artifacts from the acquired brain electrical signal data;

b) Extraction of linear and non-linear signal features; and c) Linear and non-linear discriminant analysis-based classification using pre-selected subsets of age-normalized features (z-scores).

The processor 51 is configured to implement the DSP algorithm to identify data that is contaminated by non brain-generated artifacts, such as eye movements, electromyographic activity (EMG) produced by muscle tension, spike (impulse), external noise, etc., as well as unusual electrical activity of the brain not part of the estimation of stationary background state. Artifact identification is performed using as input the signals from the five active leads Fp1, Fp2, F7, F8, AFz referenced to linked ears (A1+A2)/2, and sampled at 100 Hz. In one embodiment, incoming data epochs of 2.56 seconds (256 samples per epoch) are split into 8 basic data units (sub-epochs) of length 320 ms (32 data points per sub-epoch). Artifact identification is done on a per-sub-epoch basis and guard bands are implemented around identified artifact segments of each type. Artifact-free epochs are then constructed from at most two continuous data segments, with each data segment being no shorter than 960 ms (which corresponds to the time span of 3 contiguous sub-epochs). The resulting artifact-free data is then processed to extract signal features and classify the extracted features to provide a clinical result.

In another embodiment, signal denoising is performed using a signal processing method described in U.S. Patent Application Publication No. 2009/0263034 A1, which is incorporated herein by reference in its entirety. In one embodiment consistent with the present disclosure, the artifact identification and rejection algorithm follows the following steps:

a. Transforming the signal into a plurality of signal components;

b. Computing fractal dimension of the components;

c. Identifying noise components based on their fractal dimension;

d. Automatically attenuating the identified noise components;

e. Reconstructing a denoised signal using inverse transform.

The input analog brain electrical signal is at first digitized and then deconstructed into its constitutive coefficients using a linear or non-linear signal transformation method, such as Fast Fourier Transform, Independent Component Analysis (ICA)-based transform, wavelet transform, wavelet packet transform, etc. The fractal dimensions of the coefficients are then calculated in the transform domain, and the coefficients that have a fractal dimension higher than a preset threshold value are attenuated. The intact and re-scaled coefficients are then remixed using an inverse signal transform to generate a denoised signal, which is further processed to extract signal features and classify the extracted features.

Processor 51 is configured to execute instructions contained in memory 52 to perform an algorithm for quantitative feature extraction from processed signals. In one embodiment, the algorithm extracts various linear and non-linear features from the brain wave frequency bands: Delta (1.5-3.5 Hz), Theta (3.5-7.5 Hz), Alpha (7.5-12.5 Hz), Alpha1 (7.5-10 Hz), Alpha2 (10-12.5 Hz), Beta (12.5-25 Hz), Beta2 (25-35 Hz), Gamma (35-50 Hz), and high frequency EEG (>50 Hz). In exemplary embodiments, the features computed include, but are not limited to, absolute power, relative power, mean frequency, coherence, symmetry, fractal dimension, complex wavelet features, entropy, mutual information-based features and several statistical harmonics variables. The feature extraction algorithm takes as input a number of "artifact-free" or "denoised" epochs having a temporal length of 2.56 seconds, which corresponds to 256 samples for data sampled at 100 Hz. A full set of monopolar and bipolar features are calculated and then transformed for Gaussianity. Once a Gaussian distribution has been demonstrated and age regression applied, statistical Z transformation is performed to produce Z-scores. The Z-transform is used to describe the deviations from age expected normal values:

$$Z = \text{Probability that subject value lies within the normal range}$$

$$Z = \frac{\text{Subject Value} - \text{Norm for Age}}{\text{Standard Deviation for Age}}$$

The Z-scores are calculated for each feature and for each electrode using a database of response signals from a large population of subjects believed to be normal, or to have other pre-diagnosed conditions. In particular, each extracted feature is converted to a Z-transform score, which characterizes the probability that the extracted feature observed in the subject will conform to a normal value.

Processor 51 is further configured to perform a discriminant-based classification algorithm wherein the extracted features, or the Z-scores, are classified into one or more categories. In one embodiment, the classification is performed using one or more Linear Discriminant Functions, as described in U.S. application Ser. No. 11/195,001, U.S. Pat. No. 7,720,530, and U.S. Patent Application Publication No. 2007/0032737, which are incorporated herein by reference. In another embodiment, classification is performed by combining a subset of signal features into one or more Quadratic Discriminant Functions. The design or construction of a Discriminant Function targeting any classification task (e.g. "Normal" vs. "Abnormal" brain function) requires selection of a set of quantitative signal features K from a large available pool of features N (where N>>K). The selection of the "best" features results in the "best" classification performance, characterized by, for example, the highest sensitivity/specificity and lowest classification error rates. In illustrative embodiments, one or more quadratic classifiers are built from a training dataset through selection of a subset of features (from the set of all quantitative features), along with the construction of a mathematical function which uses these features as input and which produces as its output an assignment of the subject's data to a specific class. In some embodiments, the training dataset comprises a database of the subject's own brain electrical activity data generated in the absence or presence of an abnormal brain state. In some other embodiments, the training dataset comprises a stored population reference database for which a priori classification information is available, such as, a database comprising population normative data indicative of brain electrical activity of a first plurality of individuals having normal brain state, or population reference data indicative of brain electrical activity of a second plurality of individuals having varying levels of brain abnormalities.

The accuracy of the classifier is dependent upon the selection of features that comprise part of the specification of the classifier. Well-chosen features may not only improve the classification accuracy, but also reduce the amount and quality of training data items needed to achieve a desired level of classification performance. In an exemplary embodiment, the search for the "best" features for a binary classification task is performed using a feature selection algorithm that is referred to herein as "Simple Feature Picker" (SFP) algorithm. The SFP algorithm selects a first feature by evaluating all features in the database, and selecting the feature that provides the best classifier performance. Subsequent features are selected to give the best incremental improvement in classifier performance. The classifier performance is tested using an objective function that is directly related to classification performance. In an exemplary embodiment, the objective function used by the SFP algorithm is the area under the Receiver Operating Characteristics (ROC) curve of a Quadratic Discriminant Function, which is usually referred to as "Area Under the Curve" (AUC). For a given discriminant-based binary classifier, the ROC curve indicates the sensitivity and specificity that can be expected from the classifier at different values of the classification threshold T. Once a critical value (or threshold) T is selected, the output of the test becomes binary, and sensitivity and specificity for that particular threshold can be calculated. The ROC is the curve through the set of points: {(1-specificity(T), sensitivity(T))}, which is obtained by varying the value of the threshold T in fixed increments between 0 and 100. After the ROC curve is obtained, the area under the ROC curve (AUC) is calculated. AUC is a single number between 0 and 1, which reflects, jointly, the sensitivity and specificity of a binary classifier. Thus, AUC provides a quantitative global measure of achievable classifier performance.

In another exemplary embodiment, the SFP algorithm adds multiple features to the classifier at each iteration, calculates AUC of the resulting classifier at each iteration step, and selects the features that provide that greatest improvement in AUC.

In yet another exemplary embodiment, feature selection is performed using one or more evolutionary algorithms, such as genetic algorithm, Random Mutation Hill Climbing, and Modified Random Mutation Hill Climbing.

After a classifier is built, classification accuracy is evaluated using a testing dataset for which gold standard classification data is available. In some embodiments, the testing dataset is separate from the training set. In some other exemplary embodiments, all available data is used for both training and testing of the classifier. In such embodiments, performance of the classifier is evaluated using 10-fold and/or leave-one-out (LOO) cross-validation methods. After a classifier is built and tested for accuracy, it may be used to classify unlabeled data records as belonging to a particular class.

In an exemplary embodiment of the present disclosure, one or more Quadratic Discriminant Functions are designed and implemented for classifying patients into one of four categories related to the extent of brain dysfunction resulting from a traumatic brain injury. The four categories include: 1) normal brain electrical activity; 2) abnormal brain electrical activity consistent with non-structural injury with less severe clinical manifestations of functional injury (also referred to herein as "mild TBI"); 3) abnormal brain electrical activity consistent with non-structural injury with more severe clinical manifestations of functional injury (also referred to herein as "moderate TBI"); and 4) abnormal brain electrical activity consistent with structural brain injury.

In exemplary embodiments, the one or more quadratic classifiers are designed by first organizing the data in the training database into the four categories. The patients with normal brain electrical activity are grouped into category 1, and patients with CT scans showing structural injury are grouped into category 4 (CT+ patients). Different methods can be used for separating the categories 2 and 3 during classifier training. In some embodiments, the patients in categories 2 and 3 are distinguished using the Standardized Assessment of Concussion (SAC), which is a standardized means of objectively documenting the presence and severity of neurocognitive impairment associated with concussion. SAC cutoff score of 25 has been widely reported in the scientific literature as an indicator of concussion. In the absence of pre-injury objective data (baseline measurements), SAC score less than 25 is considered as an indicator of neurocognitive abnormalities resulting from a concussive injury. In exemplary embodiments, patients with abnormal brain electrical activity and SAC score>25 are grouped into category 2 (mild TBI), and patients with abnormal brain electrical activity and SAC score<25 are grouped into category 3 (moderate TBI).

Figure 2:
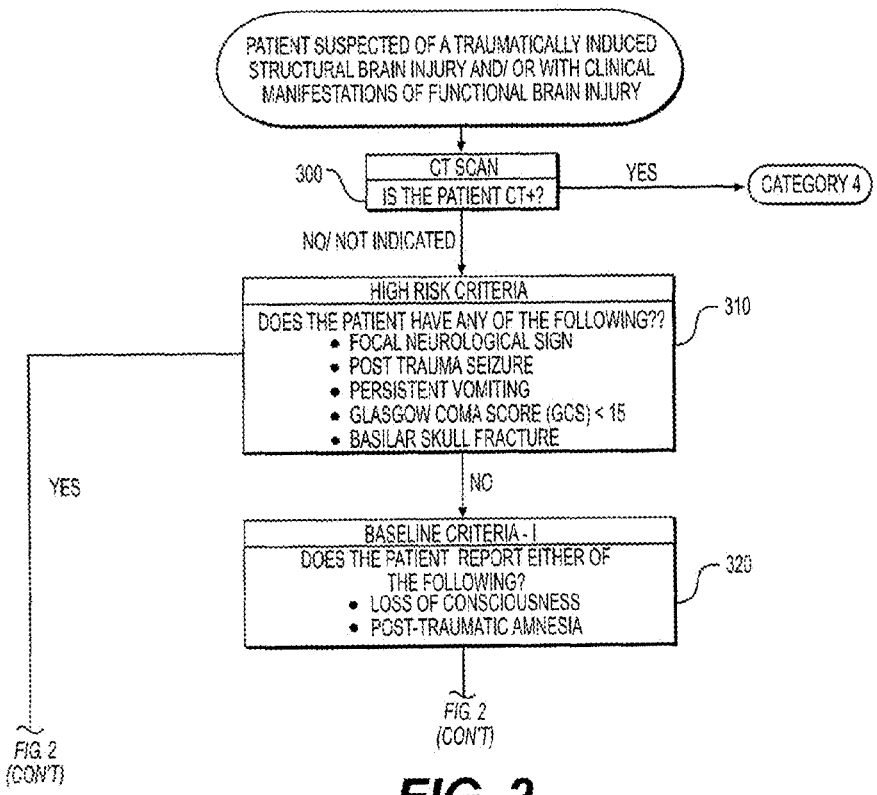
FIG. 2 is a flowchart of the process of organizing a training dataset using clinical characteristics, in accordance with an exemplary embodiment of the present disclosure.

In another exemplary embodiment, the database is organized based on a priori clinical characteristics. In an exemplary embodiment, as shown in FIG. 2, a patient suspected of a traumatically induced structural brain injury (as identified with a positive CT scan) is classified as category 4

(step 300). If the patient does not have a positive CT scan, then the patient's other clinical characteristics are evaluated. If the patient exhibits one or more of the symptoms in a high risk criteria (e.g. post-trauma seizure, persistent vomiting, basilar skull fracture, etc.) (step 310), then the patient is classified as category 3. If not, the patient is evaluated for a first set of baseline criteria associated with functional brain injury (e.g. loss of consciousness, post-traumatic amnesia, etc.) (step 320). If the patient reports any of the symptoms in the first baseline criteria, then the patient is evaluated for a second set of baseline criteria associated with functional brain injury (e.g. post-traumatic amnesia for more than 30 minutes, etc.) (step 330). If the patient reports any of the symptoms in the second set of baseline criteria, then the patient's reported symptoms and signs are further evaluated with regards to cognitive impairment and disorientation using SAC scores and Concussion Symptoms Inventory (CSI) (step 360). If the patient exhibits or reports any of the symptoms of cognitive impairment and/or disorientation, the patient is classified as category 3. If not, the patient is classified as category 2. Further, if the patient does not report any of the symptoms in the second set of baseline criteria, then the patient is classified as category 2. If, on the other hand, the patient does not report any of the symptoms of the first baseline criteria, then patient's reported symptoms are evaluated in accordance with the American Academy of Neurology (AAN) guidelines for concussion (step 340). If the patient exhibits Altered Mental Status (AMS) and at least one of the symptoms associated with concussion (e.g. dizziness, headache, nausea, etc.), then the patient is classified as category 2. If not, the patient is classified as category 1.

In exemplary embodiments, a clustering algorithm, e.g. K-means clustering, is used as a way to identify natural groupings of patients in the database based on their EEG recordings. These patient groups are then used to identify common clinical characteristics that distinguish between the groups, and these common clinical characteristic are then used to organize the database. In exemplary embodiments, the common clinical characteristics identified are also used to assign clinical classifications to patients during a clinical trial. The classification provided by the algorithm is then compared to the clinical classification to determine the accuracy of classification algorithm.

The present invention can be realized by using one or more classifiers in various orders and combinations. For example, a single multi-stage classifier might be used in place of plural classifiers in cascade or in parallel arrangements. In the example which follows, which is not considered by the inventors as limiting, the four categories related to the presence and severity of TBI are classified using three different two-way (binary) quadratic classifiers. As would be understood by a person of ordinary skill in the art, any other type of linear or non-linear classifier (for example, Linear Discriminant Analysis, Gaussian Mixture Model, etc.) could also be used to classify the categories if clinically acceptable classification performance could be achieved. In illustrative embodiments, classifier 1 (referred to herein as "1 vs. 2,3,4") is intended to separate the class of normal patients from the class of abnormal patients. Classifier 2 (referred to herein as "1,2 vs. 3,4") is intended to separate the class formed by combining the normal patients and patients with less severe functional injury from the class formed by combining patients with more severe functional injury and CT+ patients (patients with structural injury). This classifier can also be interpreted as separating the group of mild TBI patients from the group of moderate TBI patients. Classifier 3 (referred to herein as "4 vs. 3,2,1") is intended to separate the class formed by all patients who are or are expected to be CT− (patients without structural injury) from the class of CT+ patients.

Figure 3:
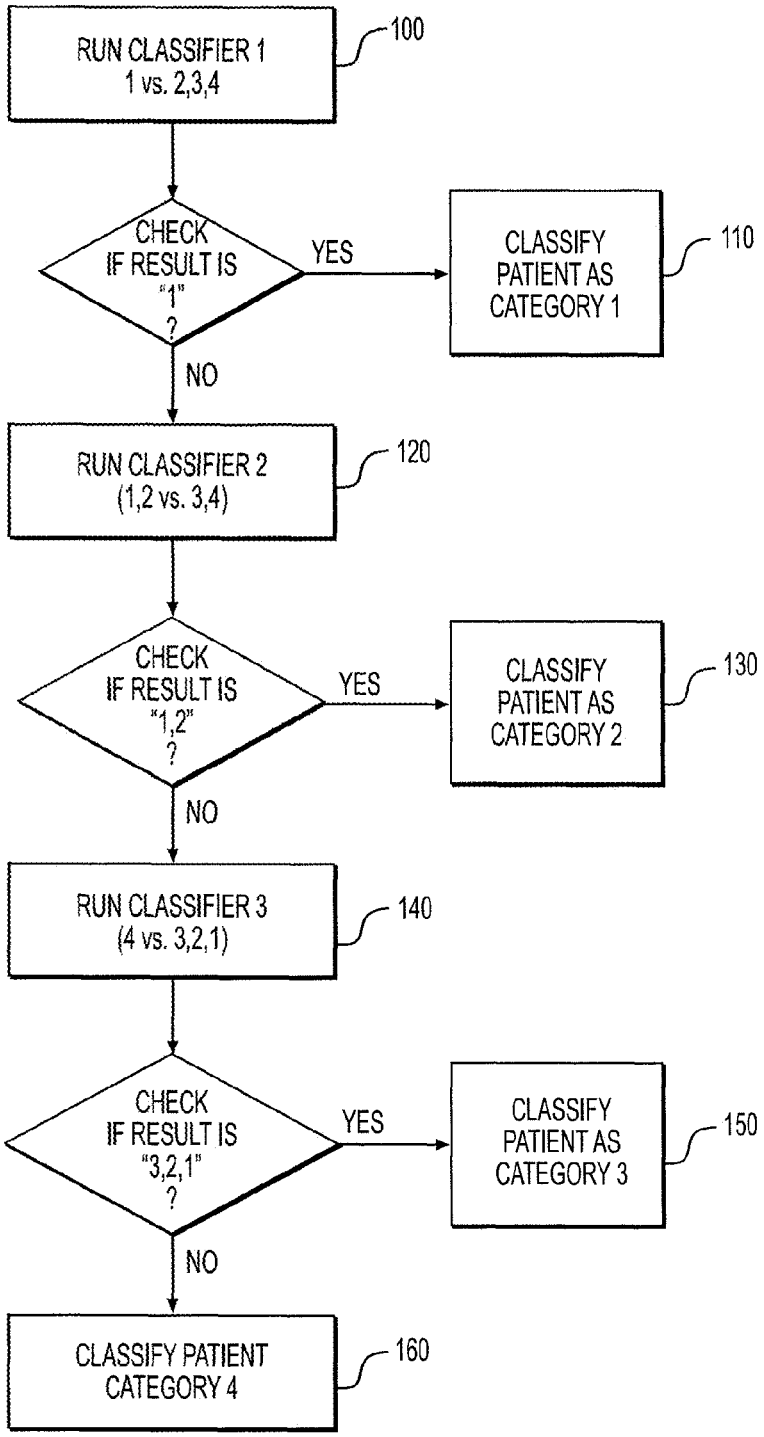
FIG. 3 is a flowchart of the classification process when three binary classifiers are combined in a cascade, in accordance with an exemplary embodiment of the present disclosure.

In one exemplary embodiment, the three binary classifiers are combined in a cascade to provide a single result at the end of the classification process, as illustrated in FIG. 3. As shown in the figure, processor 51 of neuro-assessment apparatus 10 is configured to first execute classifier 1 (step 100). If the result of classifier 1 is "1", the patient is classified as belonging to the category characterized by normal brain electrical activity (category 1) (step 110). If classifier 1 classifies a patient as belonging to the "2,3,4" class, then classifier 2 is executed (step 120). If the result of classifier 2 is "1,2," then the patient is classified as having a mild TBI (category 2) (step 130). If classifier 2 classifies a patient as belonging to the "3,4" class, then classifier 3 is executed (step 140). If the result of classifier 3 is the "3,2,1" class, then the patient is classified as having a moderate TBI (category 3) (step 150). On the other hand, if the result of classifier 3 is "4", then the patient is classified as belonging to the category characterized by structural brain injury (category 4) (step 160).

Figure 4:
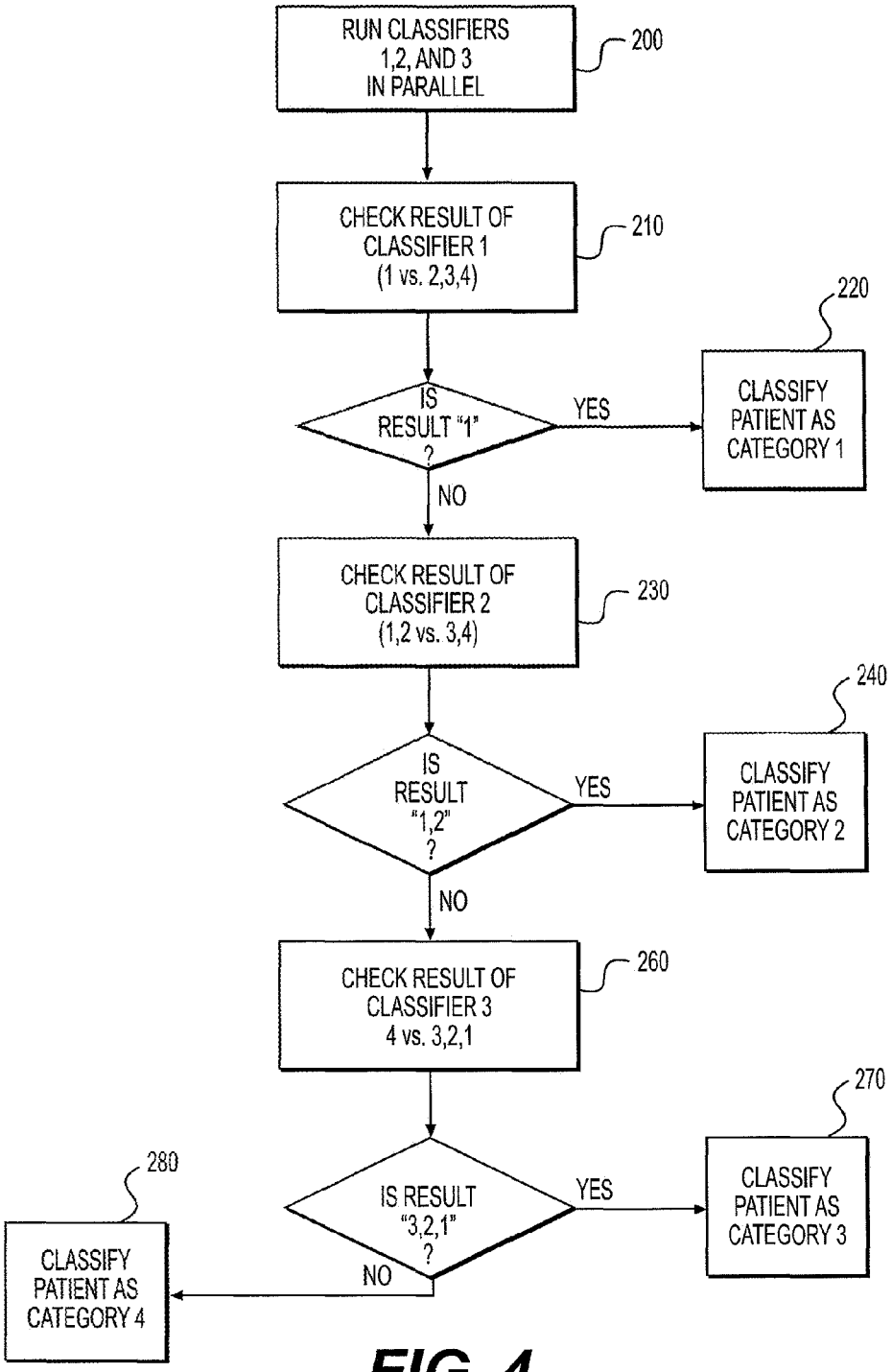
FIG. 4 is a flowchart of the classification process when three binary classifiers are executed in parallel, in accordance with an exemplary embodiment of the present disclosure.

In another exemplary embodiment, the three binary classifiers are run in parallel, and a classification result is provided based on the highest stratification or risk, as illustrated in FIG. 4. As shown in the figure, processor 51 is configured to run classifiers 1, 2 and 3 in parallel (step 200). Processor 51 first checks the classification result of classifier 1 (step 210). If the result of classifier 1 is "1", the patient is classified as belonging to the category characterized by normal brain electrical activity (category 1) (step 220). If not, the result for classifier 2 is checked (step 230). If the result of classifier 2 is the "1,2" class, then the patient is classified as having a mild TBI (category 2) (step 240). If, however, classifier 2 identifies a patient as belonging to the "3,4" class, then the result of classifier 3 is checked (step 260). If the result of classifier 3 is the "3,2,1" class, then the patient is classified as having a moderate TBI (category 3) (step 270). On the other hand, if the result of classifier 3 is "4," then the patient is classified as belonging to the category characterized by structural brain injury (category 4) (step 280).

In another exemplary embodiment, the sequence in which the three binary classifiers is executed is as follows: [1] The "4 vs. 3,2,1" classifier is executed to discriminate between patients in category 4 and all other categories combined. For a patient identified as a "4", the classification process is over and the results are displayed; if not classified as a "4", then [2] the "1 vs. 2,3,4" classifier is executed to discriminate patients in category 1 from the balance of the patients (categories 2, 3, or 4). For a patient identified as a "1", the classification process is complete; if not classified as a "1", then [3] the "1,2 vs. 3,4" classifier is used to discriminate patients in categories 2 and 3. This sequence allows stratification of risk by classifying and removing the highest risk (CT+) patients first.

In yet another embodiment, processor 51 is configured to execute the three binary classifiers independently of each other, and provide three separate classification results along with some objective performance measures for each classifier. The classification decision is then driven by the clinician based on the classification performance and other clinically relevant factors, such as, symptoms presented, history of injury, etc.

In exemplary embodiments, the performance of the three classifiers are tested by computing the specificity (true negative rate) and sensitivity (true positive rate) for each of the four categories. ROC curve is used to illustrate quantitatively the performance of each binary classifier, and to compute the specificity and sensitivity values. This allows, for example, a threshold T to be selected that ensures that a conservative classification is always assigned according to the appropriate stratification of risk for the categories being separated. In another embodiment, instead of using a threshold on the ROC curve to decide which category the patient falls in, a likelihood of belonging to both categories is computed for the three classifiers when executed in parallel. The benefit of this approach is that information from all three classifiers is used for all patients.

Figure 5A:
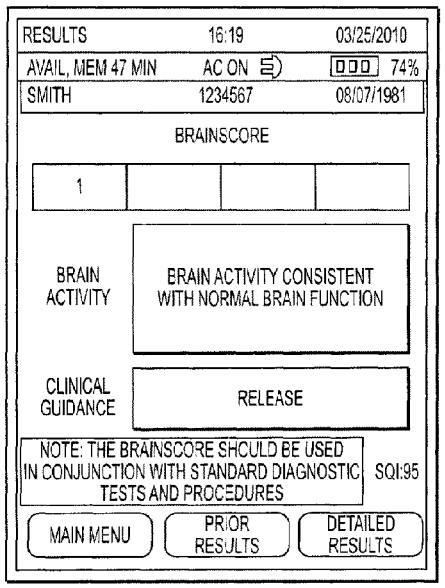
FIGS. 5A-5D illustrate the clinical guidance provided by a neuro-assessment apparatus for each category related to the extent of TBI, in accordance with an exemplary embodiment of the present disclosure.
Figure 5B:
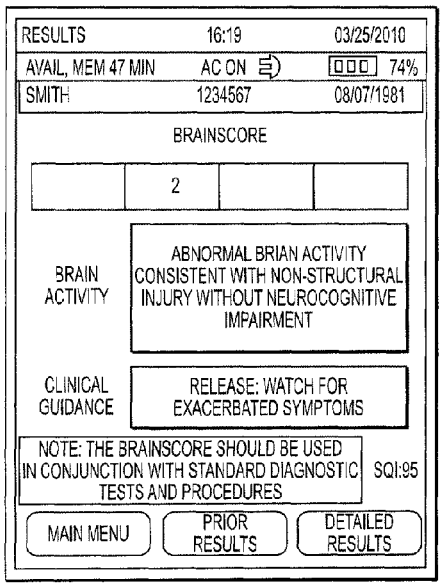
Figure 5C:
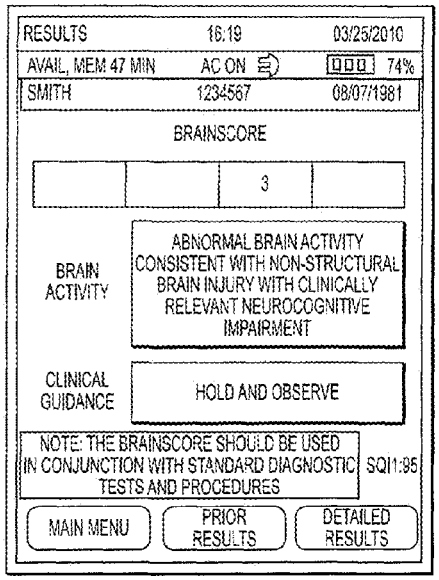
Figure 5D:
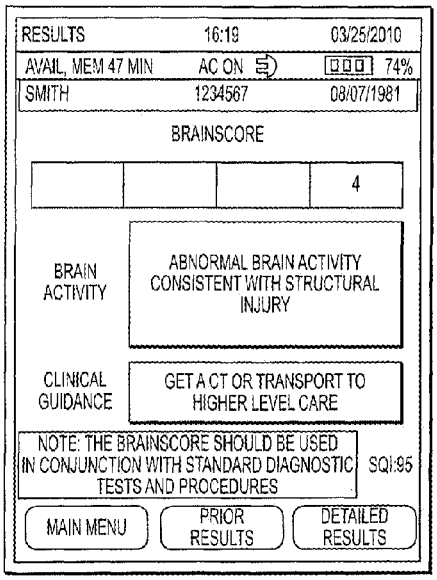

In an embodiment consistent with the present disclosure, processor 51 is configured to provide clinical guidance to attending medical personnel, such as an ER physician, a triage nurse, or an emergency response technician, in accordance with the classification results. The clinical guidance may be displayed on a screen of user interface 46 or display 44, as illustrated in FIGS. 5A-5D. In exemplary embodiments, if a patients is classified into category 1, user interface 46 displays a clinical guidance that the patient is normal and may be released if other assessments (symptoms, neurological exam, etc.) are normal (FIG. 5A). If the patient is classified into category 2, user interface 46 displays a message suggesting that the patient may be released if other assessments are normal, but recommends that a reevaluation should be scheduled to check for exacerbated symptoms (FIG. 5B). Similarly, if the patient is classified into category 3, user interface 46 displays a message suggesting that the clinician should hold the patient for close medical observation and further evaluations (possibly a CT scan) to rule out serious brain injury (FIG. 5C). If the patient is classified into category 1, user interface 46 provides a clinical guidance to obtain a CT scan immediately and/or transport the patient to higher level care (FIG. 5D). In another exemplary embodiment, the clinical guidance associated with the categories is not displayed on the user interface 46, but is included in a device manual that the clinician may refer to.

In yet another embodiment, the presence and/or severity of TBI may be indicated using a color-coded display. A red light could be illuminated on user interface 46 if a patient is classified as category 4, a yellow light could be illuminated if a patient is classified as either category 1 or 2, and a green light could be illuminated if a patient is classified as category 1. The color-coded indication provides a simple, easy-to-use and easy-to-read means for quickly determining the presence and severity of TBI in a patient.

In certain embodiments, user interface 46 conveys a variety of additional data, including, but not limited to, intermediate analysis results, usage settings, patient information, battery life of the handheld device, etc. Additional, in some embodiments, memory 52 of neuro-assessment apparatus 10 contains interactive instructions for using and operating the device that is displayed on a screen of display 44 or on user interface 46. The instructions may comprise an interactive feature-rich presentation including a multimedia recording providing audio/video instructions for operating the device, or alternatively simple text, displayed on the screen, illustrating step-by-step instructions for operating and using the device. The inclusion of interactive instructions with the device eliminates the need for extensive training for use, allowing for deployment and use by persons other than medical professionals.

Neuro-assessment apparatus 10 can be a standalone system or can operate in conjunction with a mobile or stationary device to facilitate display or storage of data, and to signal healthcare personnel when therapeutic action is needed, thereby facilitating early recognition of emergency conditions. Mobile devices can include, but are not limited to, handheld devices and wireless devices distant from, and in communication with, the neuro-assessment apparatus. Stationary devices can include, but are not limited to, desktop computers, printers and other peripherals that display or store the results of the neurological evaluation. In an exemplary embodiment, the neuro-assessment apparatus stores each patient file, which includes a summary of the session and test results, on a removable memory card 47, such as compact flash (CF) card. The user can then use the memory card 47 to transfer patient information and procedural data to a computer, or to produce a printout of the data and session summary. In another embodiment, results from the processor 51 are transferred directly to an external mobile or stationary device to facilitate display or storage of data. For example, the results from the processor 51 may be displayed or stored on a PC 48 connected to the base unit 42 using a PC interface, such as an USB port, IRDA port, BLUETOOTH® or other wireless link. In yet another embodiment, the results can be transmitted wirelessly or via a cable to a printer 49 that prints the results to be used by attending medical personnel. In exemplary embodiments, as discussed earlier in this disclosure, user interface 46 is configured to communicate patient information, treatment guidance and/or procedural data to an attending medical personnel, such as an ER physician, a triage nurse, or an emergency response technician.

Neuro-assessment apparatus 10 is designed for near-patient testing (i.e. point-of care) in emergency rooms, ambulatory setting, and other field applications. The neuro-assessment apparatus is intended to be used in conjunction with CT scan, MRI or other imaging studies to provide complementary or corroborative information about a patient's neurological condition. The key objective of point-of-care neuro-assessment is to provide fast results indicating the severity of a patient's neurological condition, so that appropriate treatment can be quickly provided, possibly leading to an improved overall clinical outcome. For example, the neuro-assessment device may be used by an EMT, ER nurse, or any other medical professional during an initial patient processing in the ER or ambulatory setting, which will assist in identifying the patients with emergency neurological conditions. It will also help ER physicians in corroborating an immediate course of action, prioritizing patients for imaging, or determining if immediate referral to a neurologist or neurosurgeon is required. This in turn will also enable ER personnel to optimize the utilization of resources (e.g., physicians' time, use of imaging tests, neuro consults, etc.) in order to provide safe and immediate care to all patients.

In addition, neuro-assessment apparatus 10 is designed to be field-deployable, that is, it can be used in locations far removed from a full-service clinic—for example, in remote battlefield situations distant from military healthcare systems, during sporting events for indentifying if an injured athlete should be transported for emergency treatment, at a scene of mass casualty in order to identify patients who need critical attention and immediate transport to the hospital, or at any other remote location where there is limited access to well-trained medical technicians.

Example

Application of Three Binary Classifiers for Differential Classification of Extent of Brain Dysfunction Three separate binary classifiers were used to statistically place subjects in one of four categories related to the extent of brain dysfunction following a head injury. A large population of controls (n=255) and patients who sustained closed head injuries (n=358) were evaluated using neuro-assessment apparatus 10, and were rated on the Standard Assessment of Concussion (SAC). Ten minutes of eyes closed brain electrical activity was recorded in a blinded fashion using electrodes placed on the forehead at standardized locations. A denoising algorithm was used to identify and remove non-brain related activity. Features extracted included both linear and non-linear measures of brain electrical activity, including, power, mean frequency, inter- and intra-hemispheric symmetry and coherence, complexity and connectivity. All features were then transformed relative to age expected normal values. A mathematically selected subset of these features were combined in three quadratic classifier functions to statistically place subjects in one of four categories. The classification functions were designed using the "Simple Feature Picker" (SFP) algorithm. Classification performance was expressed in terms of sensitivity and specificity using area under the ROC curve (AUC) as an objective function.

As described earlier in this disclosure, category 1 relates to normal brain activity, category 2 relates to mild TBI, category 3 relates to moderate TBI, and category 4 relates to structural brain injury requiring immediate triage. Results show high accuracy in separating the four categories from each other, as shown in Table. 1 (FIG. 6). Category 4 was separated from all other categories with a sensitivity of 91% and a specificity of 85% (AUC=0.93), category 1 was separated from all others with a sensitivity of 81% and a specificity of 80% (AUC=0.83), and category 3 and 4 (those needing further observation or immediate triage) were separated from categories 2 and 1 (those who could be considered to be returned to activity, with or without recommendation for follow-up) with a sensitivity of 80% and specificity of 79% (AUC=0.86). In sum, the study demonstrated high sensitivity and specificity in identification of TBI requiring immediate triage, as well as in the separation of those with head injuries that have different levels of brain dysfunction.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. An apparatus for assessment of traumatic brain injury in a patient, comprising:

a patient sensor comprising at least one neurological electrode; and a handheld base unit operatively coupled to the patient sensor, the base unit comprising:

a digital signal processor configured to perform automatic identification and removal of artifacts from brain electrical signals acquired by the at least one neurological electrode, extract one or more features from the acquired brain electrical signals, and execute at least one classification function to classify the patient into one of [four] *a plurality of* categories indicative of the presence and severity of traumatic brain injury;

wherein *the* at least one classification function is designed using a training database comprising a population of controls and patients who [reportedly] sustained closed head injuries and the training database is organized using Standard Assessment of Concussion (SAC) scores.

2. The apparatus of claim 1, wherein the at least one classification function comprises at least three classification functions.

3. The apparatus of claim 2, wherein the digital signal processor is configured to execute the at least three classification functions in cascade.

4. The apparatus of claim 2, wherein the digital signal processor is configured to execute the at least three classification functions in a sequence, the sequence comprising the steps of:

executing a first classification function designed to classify patients with structural brain injury from patients who are normal or have only functional brain injury;

executing a second classification function designed to classify normal patients from patients having structural and/or functional brain injury; and executing a third classification function designed to classify patients with two separate grades of functional brain injury.

5. The apparatus of claim 2, wherein the three classification functions comprise:

a first classification function designed to classify patients with structural brain injury from patients who are normal or have only functional brain injury;

a second classification function designed to classify normal patients from patients having structural and/or functional brain injury; and a third classification function designed to classify patients with severe and less severe manifestations of functional injury when no structural injury is present.

6. The apparatus of claim 1, wherein the at least one classification function comprises at least two classification functions.

7. The apparatus of claim 6, wherein the digital signal processor is configured to execute the at least two classification functions in parallel.

8. The apparatus of claim 7, wherein the digital signal processor is configured to execute the at least two classification functions independent of each other.

9. The apparatus of claim 8, wherein the base unit further comprises a user interface for displaying one or more classification performance measures to enable a clinician to make a decision about a category of the patient.

10. The apparatus of claim 6, further comprising a multi-stage classifier, wherein the at least two classification functions are performed by the multi-stage classifier.

11. The apparatus of claim 1, wherein the base unit further comprises a display unit for providing an indication of the presence and severity of traumatic brain injury.

12. The apparatus of claim 11, wherein the display unit displays the category that the patient is classified into.

13. The apparatus of claim 1, wherein the training database is organized using one or more clinical characteristics.

14. The apparatus of claim 1, wherein the one or more features comprise linear and/or non-linear quantitative features.

15. The apparatus of claim 1, wherein the [four] *plurality of* categories comprise:

abnormal brain electrical activity consistent with structural brain injury;

abnormal brain electrical activity consistent with non-structural injury with severe clinical manifestations of functional injury;

abnormal brain electrical activity consistent with non-structural injury with less severe manifestations of functional injury; and normal brain electrical activity.

[16. A method for assessment of traumatic brain injury in a patient, comprising the steps of:

connecting at least one neurological electrode to the patient's forehead to acquire brain electrical signals; and providing a base unit operatively connected to the at least one neurological electrode to process the acquired brain electrical signals;

wherein the base unit comprises a digital signal processor configured to perform automatic identification and removal of artifacts from brain electrical signals acquired by the at least one neurological electrode, extract one or more features from the acquired brain electrical signals, and execute at least one classification function to classify the patient into one of four categories indicative of the presence and severity of traumatic brain injury, wherein the at least one classification function is designed using a training database comprising a population of controls and patients who reportedly sustained closed head injuries and the training database is organized using Standard Assessment of Concussion (SAC) scores.]

[17. The method of claim 16, wherein the at least one classification function comprises at least three classification functions.]

[18. The method of claim 17, wherein the digital signal processor is configured to execute the at least three classification functions in cascade.]

[19. The method of claim 17, wherein the digital signal processor is configured to execute the at least three classification functions in a sequence, the sequence comprising the steps of:

executing a first classification function designed to classify patients with structural brain injury from patients who are normal or have only functional brain injury;

executing a second classification function designed to classify normal patients from patients having structural and/or functional brain injury; and executing a third classification function designed to classify patients with two separate grades of functional brain injury but no structural injury.]

[20. The method of claim 17, wherein the three classification functions comprise:

a first classification function designed to classify patients with structural brain injury from patients who are normal or have only functional brain injury;

a second classification function designed to classify normal patients from patients having structural and/or functional brain injury; and a third classification function designed to classify patients with severe and less severe manifestations of functional injury when no structural injury is present.]

[21. The method of claim 16, wherein the at least one classification function comprises at least two classification functions.]

[22. The method of claim 21, wherein the digital signal processor is configured to execute the at least two classification functions in parallel.]

[23. The method of claim 21, wherein the digital signal processor is configured to execute the at least two classification functions independent of each other.]

[24. The method of claim 23, wherein the base unit further comprises a user interface for displaying one or more classification performance measures to enable a clinician to make a decision about a category of the patient.]

[25. The method of claim 21, wherein the at least two classification functions are performed by the multi-stage classifier.]

[26. The method of claim 16, wherein the base unit further comprises a display unit for providing an indication of the presence and severity of traumatic brain injury.]

[27. The method of claim 26 wherein the display unit displays the category that the patient is classified into.]

[28. The method of claim 16, wherein the four categories comprise:

abnormal brain electrical activity consistent with structural brain injury; abnormal brain electrical activity consistent with non-structural injury with severe clinical manifestations of functional injury; abnormal brain electrical activity consistent with non-structural injury with less severe manifestations of functional injury; and normal brain electrical activity.]

[29. The method of claim 16, wherein the training database is organized using a series of clinical characteristics.]

[30. The method of claim 16, wherein the training database is used for testing performance of the three classification functions using cross-validation.]

[31. The method of claim 30, wherein said cross-validation is leave-one-out cross-validation.]

[32. The method of claim 16, wherein the one or more features comprise linear and/or non-linear quantitative features.]

[33. The method of claim 16, wherein the one or more quantitative features comprise mutual information features.]

[34. The method of claim 16, wherein the at least one classification function is designed using an evolutionary classifier builder algorithm.]

[35. The method of claim 34, wherein the evolutionary classifier builder algorithm comprises a genetic algorithm.]

[36. The method of claim 34, wherein the evolutionary classifier builder algorithm comprises Modified Random Mutation Hill Climbing algorithm.]

* * * * *